United States Patent [19]

Chollet

[11] Patent Number: 5,024,690

[45] Date of Patent: Jun. 18, 1991

[54] SEED TREATMENT COMPOSITIONS

[75] Inventor: Charles C. Chollet, Caldwell, Id.

[73] Assignee: Snake River Chemicals, Inc., Caldwell, Id.

[21] Appl. No.: 437,276

[22] Filed: Nov. 15, 1989

Related U.S. Application Data

[60] Division of Ser. No. 290,236, Dec. 22, 1988, which is a continuation-in-part of Ser. No. 859,240, May 7, 1986, abandoned, which is a continuation of Ser. No. 696,443, Jan. 30, 1985, abandoned.

[51] Int. Cl.$^5$ .................. A01N 25/00; C05F 11/00
[52] U.S. Cl. ............................................. 71/77; 71/23
[58] Field of Search .................. 71/77, 23, 24

[56] References Cited

U.S. PATENT DOCUMENTS

| | | | |
|---|---|---|---|
| 2,314,091 | 3/1943 | Jones | 71/77 |
| 2,782,241 | 2/1957 | Gray et al. | 568/716 |
| 2,838,877 | 6/1958 | Working | 47/58 |
| 2,845,450 | 7/1958 | Anderson et al. | 560/268 |
| 2,909,869 | 10/1959 | Dresser | 71/1 |
| 3,370,957 | 2/1968 | Wagner et al. | 514/365 |
| 3,561,943 | 2/1971 | Gay et al. | 71/9 |
| 3,607,211 | 9/1971 | Cole et al. | 71/1 |
| 3,645,714 | 2/1972 | Heming et al. | 71/23 |
| 3,813,236 | 5/1974 | Allan | 71/79 |
| 3,867,324 | 2/1975 | Clendinning et al. | 523/126 |
| 3,901,838 | 8/1975 | Clendinning et al. | 523/126 |
| 3,940,257 | 2/1976 | Sherwin et al. | 71/23 |
| 3,966,708 | 6/1976 | Casebier et al. | 71/23 |
| 3,970,691 | 7/1976 | Sears et al. | 562/32 |
| 4,067,716 | 1/1978 | Sterrett | 71/24 |
| 4,145,206 | 3/1979 | Ford | 71/23 |

FOREIGN PATENT DOCUMENTS 2432432  1/1975  Fed. Rep. of Germany .......... 71/23

OTHER PUBLICATIONS

Hartley et al., *The Agrochemicals Handbook*, A391, (The Royal Soc. Chem., 1983).

Secor et al., *Valley Potato Grower*, pp. 27–28, (Nov. 1987).

Chollet, *Potato Grower of Idaho*, pp. 42–43, (Jan. 1985).

*Primary Examiner*—Richard L. Raymond
*Assistant Examiner*—Brian Bembenick
*Attorney, Agent, or Firm*—Willian Brinks Olds Hofer Gilson & Lione

[57] ABSTRACT

Methods of using comminuted Alder bark as a stimulator of seed germination and growth media comprising comminuted Alder bark are disclosed. Also disclosed are seed treatment dusts comprising an active ingredient, a diluent material and comminuted Alder bark and methods of using these dusts. The active ingredients include fungicides, insecticides and other pesticides. The diluent materials used include clays and talcs.

6 Claims, No Drawings

SEED TREATMENT COMPOSITIONS

This is a division of application Ser. No. 07/290,236, filed Dec. 22, 1988, which is a continuation-in-part of Applicant's pending application Ser. No. 06/859,240, filed May 7, 1986, now abandoned which was a continuation of application Ser. No. 06/696,443, filed Jan. 30, 1985, now abandoned.

BACKGROUND OF THE INVENTION

It has long been known that the dusting of seeds prior to planting with seed treatment dusts composed of an active ingredient and one or more diluent materials would improve crop yields. The active ingredients commonly used include fungicides, insecticides, and other pesticides. The diluent materials used include clays, talcs and comminuted Douglas Fir bark.

The active ingredient of the seed treatment dust protects the newly planted seed and its developing root system from attacks by harmful organisms found in the soil during the germination period. The germination period is critical because the events that occur during this period determine, to a great extent, the health and productivity of the plant that grows from the seed. The longer a seed remains in the ground before it germinates, the more vulnerable it becomes to attack by fungi and by other soil-borne pathogens and insects. A seed attacked by soil-borne organisms is less likely to produce a healthy plant. Indeed, such a seed may not produce a plant at all.

If, however, a seed germinates quickly and is protected from attack by soil-borne organisms during the germination period, there is much less chance that the plant will become diseased or will die if it does become diseased. Since the active ingredients used in seed treatment dusts protect the seed from attack by soil-borne organisms, seeds dusted with dusts containing an active ingredient have an increased chance of producing a healthy, productive plant.

The diluent materials used in seed treatment dusts act to dry seeds. Wet seeds are susceptible to attack by bacteria while they are stored awaiting planting, and a bacterial infection may weaken the seed. A weakened seed will, in turn, produce an unhealthy plant or will not produce a plant at all.

The combination of the drying effect of the diluent materials and the fungicidal or other activity of the active ingredient protects the seed during the period prior to planting and during the germination period. Seeds thus protected are much more likely to produce high crop yields.

Seeds which are dusted include the seeds of grains, legumes, onions, tubers and flowers. In particular, the dusting of tuber seeds such as potato seeds is very desirable for the production of good crops.

Potato seeds are prepared for planting by cutting a potato into several parts. The potato seed pieces are then loaded into trucks or bags and stored until planting.

When the potato is cut, the cut sides of the potato are moist. The potato secretes a substance called suberin which begins to heal the cut surface of the potato in six to eight hours if the potato surface can dry during this time. Since the potato seed pieces are piled into bags or trucks after cutting, they would, under these circumstances, remain wet for an extended period of time. These wet conditions promote bacterial growth. Further, since the suberin cannot heal the cut surface of the potato while it is wet, the bacteria can more easily gain access to the potato seed and start to decay the seeds. Seeds thus attacked by bacteria may be weakened before they are planted. Potato seeds and their newly developing root systems are ordinarily susceptible to insects, to fungi and to other soil-borne pathogens, but a weakened seed is particularly susceptible to these harmful organisms.

If the potato seeds are dusted immediately after they are cut, the diluent materials dry the potato seeds thereby allowing the suberin to heal the cut surfaces of the potato seeds and removing an environment conducive to bacterial growth. The dusted seeds are, consequently, less likely to be weakened by bacterial decay before being planted. Further, the active ingredient in the seed treatment dust will protect the potato from attack by harmful soil-borne organisms after planting.

As mentioned above, one of the diluent materials in use is comminuted Douglas Fir bark. Comminuted Douglas Fir bark is an excellent diluent material since it is a very effective drying agent. One problem with the use of comminuted Douglas Fir bark is that it contains lignin slivers as do all coniferous tree barks, and some workers using seed treatment dusts containing comminuted Douglas Fir bark suffer minor throat, nasal and skin irritation from the lignin slivers. Another problem is that Douglas Fir bark is much more expensive than the clay and talc diluents.

SUMMARY OF THE INVENTION

According to the invention, there are provided methods of using comminuted Alder bark as a stimulator of germination. In one method, seeds are planted in a growth medium comprising comminuted Alder bark, and the growth medium is placed into an environment conducive to germination. In a second method, seeds are dusted with a material comprising comminuted Alder bark and are then planted. Growth media comprising comminuted Alder bark are also disclosed.

There are also provided, according to the invention, seed treatment dusts comprising:
 (a) an active ingredient;
 (b) a diluent material; and
 (c) comminuted Alder bark.

Methods of using these dusts are also disclosed.

Comminuted Alder bark functions in these seed treatment dusts as a diluent material. It is, however, a unique diluent material because it has been found, quite unexpectedly, that comminuted Alder bark, alone or in combination with other diluent materials and active ingredients, acts as an excellent stimulator of germination as compared to other diluent materials including comminuted Douglas Fir bark, clay and talc.

The use of comminuted Alder bark in seed treatment dusts also overcomes the problems presented by the use of comminuted Douglas Fir bark in such dusts. Workers using dusts containing comminuted Alder bark do not experience the minor throat, nasal and skin irritation caused by lignin slivers since the bark of the Alder tree does not contain lignin. Comminuted Alder bark is also considerably less expensive than comminuted Douglas Fir bark.

DETAILED DESCRIPTION OF PRESENTLY PREFERRED EMBODIMENTS

The general properties of the comminuted Alder bark useful for practicing all embodiments of the invention will first be described. Then, the use of comminuted Alder bark to stimulate germination and growth media comprising comminuted Alder bark will be described. Finally, the composition of seed treatment dusts comprising comminuted Alder bark and methods of treating seeds with such dusts will be described.

DESCRIPTION OF COMMINUTED ALDER BARK

The comminuted Alder bark preferred for practicing the invention was purchased from Menasha Corporation, Eugene, Oreg. (sold under the name Modal) or from Asbury Waldron Inc., Marysville, Wash. (sold under the name Walderfil). Comminuted Alder bark from either source is prepared by first pulverizing bark which has been stripped from the Alder trees during the processing of the trees at the lumber mill until the particles are very small. Comminuted bark useful for practicing the invention preferably has the consistency of a powder or dust. After the bark is pulverized, it is dried to reduce the moisture content to preferably from about 6 to about 11% by weight.

Uniform particle size of the pulverized bark is important, and comminuted Alder bark which meets the following standards is preferred: 100% of the particles will pass through a 40 mesh screen, 98% of the particles will pass through a 100 mesh screen, and 91 to 97% of the particles will pass through a 200 mesh screen. Comminuted Alder bark meeting these standards is also preferred because it has the consistency of a powder or dust.

Although comminuted Alder bark having these characteristics is preferred, comminuted Alder bark of different particle sizes, different moisture contents and different consistencies may be used to practice the invention. In particular, in the growth media of the invention, it is anticipated that these characteristics can be varied substantially.

STIMULATION OF GERMINATION BY COMMINUTED ALDER BARK

EXAMPLE 1

There are two types of Alder bark. Light Alder bark is bark which has laid on the log or which has been stored in piles after being stripped off the log for less than three months, preferably for less than six weeks, before being processed into comminuted bark as described above. Dark Alder bark is Alder bark which has remained on the log or which has been stored in piles after being stripped off the log for more than three months.

Derkwin wheat seeds were planted in growth media composed of: (1) 100% comminuted Douglas Fir bark, (2) 100% comminuted light Alder bark or (3) 100% comminuted dark Alder bark, and the growth media containing the seeds were placed into an enclosed growth chamber where they were maintained under identical conditions of temperature and humidity. The seeds planted in the three media were observed for fourteen days after planting.

Surprisingly, it was found that the seeds planted in the light Alder bark emerged 5 days before those planted in the Douglas Fir bark, and the seeds planted in the dark Alder bark emerged 2 days before those planted in the Douglas Fir bark. Further, at the end of fourteen days, the wheat planted in the light Alder bark was on an average 2.75 inches tall, wheat planted in the dark Alder bark was on an average 2.00 inches tall, and wheat planted in the Douglas Fir bark was on an average 1.75 inches tall. In addition, wheat planted in the light or in the dark Alder bark was judged to exhibit better growth vigor compared to the wheat planted in the Douglas Fir bark.

The earlier germination of seeds and the better health and growth of plants in the two Alder bark media as compared to the Douglas Fir bark medium was unanticipated. These properties of the comminuted Alder bark, however, make it well suited for applications where early germination and good growth of plants is desired. Further, in view of the results of this experiment, comminuted light Alder bark is preferred for practicing the invention.

EXAMPLE 2

Potato seeds were cut and allowed to dry for 24 hours. After drying, the seeds were planted in growing media composed of: (1) 100% comminuted light Alder bark, (2) 100% comminuted Douglas Fir bark or (3) 100% Cyprus Talc BT 200.

Cyprus Talc BT 200 is a talc having the following chemical composition:

MgO: 30%
$SiO_2$: 60%
$Al_2O_3$: 0.5%
CaO: 2%
$Fe_2O_3$: 2%
Loss on ignition or oxidation: 5.5%

It contains 0.2% absorbed moisture, and the median particle size is 8 microns (range of from about 1 to about 74 microns). The loose material has a density of 28±2 lbs/ft.$^3$, and the tapped material has a density of 60±2 lbs/ft.$^3$. A mineral analysis of Cyprus Talc BT 200 revealed that it contained 94% talc, 2% dolomite, 2% calcite and 2% quartz. It was purchased from Cyprus Industrial Minerals Co., 555 South Flower Street, Los Angeles, Calif. 90071.

The planted seeds were observed daily, and the following results were obtained:

| Medium | Days After Planting Until Emergence of Plant |
|---|---|
| 100% Alder bark | 21 |
| 100% Douglas Fir bark | 23–24 |
| 100% Cyprus Talc BT 200 | 23–24 |

EXAMPLE 3

Different groups, each containing fifteen Russet Burbank potato seeds, were dusted with one of the following four dusts:

| Dust A: | ½% Thiabendazole |
| | 25% Comminuted light Alder bark |
| | 48% Cyprus Talc BT 200 |
| | 24% Zeolite |
| Dust B: | 100% Cyprus Talc BT 200 |
| Dust C: | 100% Comminuted Douglas Fir bark |
| Dust D: | ½% Thiabendazole |
| | 58% Cyprus Talc BT 200 |
| | 42% Zeolite |

Thiabendazole is a systemic fungicide whose chemical name is 2-(4-thiazolyl)-benzimidazole which was purchased as a 98% pure material from Merck & Co., Rahway, N.J.

Zeolite is a clay which was purchased from Teague Mineral Products, Adrian, Oreg. Zeolite has the following chemical composition:

$SiO_2$: 69.60%
$Al_2O_3$: 11.30%
$K_2O$: 5.20%
$Fe_2O_3$: 1.84%
$Na_2O$: 1.04%
$CaO$: 1.00%
$MgO$: 0.36%
$TiO_2$: 0.30%
$BaO$: 0.20%
$MnO_2$: 0.01%
$P_2O_5$: 0.01%
$SiO_3$: 0.01%
$PbO$: 0.01%

The dusted potato seeds were planted immediately after dusting, and the potato seeds were observed daily during the germination period to ascertain the day of emergence of the seedlings. The following results were obtained:

| Dust | Days After Planting Until Emergence of Plant |
| --- | --- |
| A | 28 |
| B | 35 |
| C | 35 |
| D | 31 |

EXAMPLE 4

Three to four bounds of 100% comminuted light Alder bark were mixed in the planter box of an automated planting device with 100 pounds of bean seeds until the bean seeds were evenly dusted with the Alder bark. The dusted bean seeds were planted. Other bean seeds were planted without being dusted with comminuted Alder bark. The beans were planted at 100 pounds of beans per acre. Ten acres in the middle of a forty acre field were planted with dusted seed, and the remaining thirty acres were planted with undusted seed. During the early growing season the plants which germinated from the dusted seeds were more vigorous and healthier than the plants which germinated from the undusted seeds.

EXAMPLE 5

Three pounds of comminuted light Alder bark were mixed in a grain drill with 100 pounds of barley seed. The barley was planted at the rate of 120 pounds per acre. Observations during the early growing season showed that the barley which germinated from the Alder bark treated seeds grew faster and taller than the barley which germinated from the untreated barley.

EXAMPLE 6

Norgold variety potato seeds were dusted with the following fungicide dusts:

| Dust A: | 2.5% Topsin-M<br>25% Comminuted light Alder bark<br>48% Cyprus Talc BT 200<br>24% Zeolite |
| --- | --- |
| Dust B: | 5% Captan 90 and<br>95% Cyprus Talc BT 200. |

Topsin-M is a systemic fungicide whose chemical name is thiophanate-methyl, and whose true chemical names are 4,4'-o-phenylenebis(3-thioallophanate) and dimethyl-(1,2-phenylenebis(iminocarbonothioyl) bis-carbamate. Topsin-M having a guaranteed analysis of 94.5% was purchased from Gustafson, Dallas, Tex.

Captan 90 is a fungicide having the chemical name N-(trichloromethylthio)-4-cyclohexene-1,2-dicarboximide which was purchased as an 85.1% pure material from either Chevron Chemical Co., 575 Market St., San Francisco, Calif. 94105 or Stauffer Chemical Co., Agricultural Chemicals Division, Westport, Conn. 06881.

It was found that seeds treated with Dust A emerged three to four da-s earlier and with over 30% greater stand count (the number of plants germinated and growing in a given area) than those treated with Dust B. It was also noted that after making counts of the number of stems on individual plants in ten 50-foot rows that the plants from seeds treated with Dust A had an average of 3.26 stems per plant as compared with 2.86 stems per plant for plants from seeds treated with Dust B. In order to obtain maximum crop yield, the plants should have three to four stems per plant.

EXAMPLE 7

A study was conducted to determine the germination and growth characteristics of wheat treated with three different seed treatment compositions containing 0.5% Thiabendazole. The study was performed as follows. First, six ounces of washed sand were placed in the bottom of containers B inches in diameter and 1 inch in depth. One hundred Stevens variety wheat seeds were next distributed uniformly on top of the sand, and six ounces of one of the following materials was placed uniformly over the seeds:

| Material | Composition |
| --- | --- |
| A | 0.5% Thiabendazole<br>99.5% Cyprus Talc BT 200 |
| B | 0.5% Thiabendazole<br>99.5% Comminuted Douglas Fir Bark |
| C | 0.5% Thiabendazole<br>99.5% Comminuted Alder Bark |

A total of ten container were used to test each material, for a total of 30 containers, 100 seeds per container.

After the addition of materials A-C to the containers, four ounces of water were added to each container. In addition, each of the thirty total containers received two ounces of water each day during the study beginning one day after the planting of the seeds.

The temperature was between 50° and 70° F. during the period of the test. Indirect sunlight was available to the plants during the germination and growth period.

Sixteen days after the planting of the seeds, all plants emerging from the growth medium were counted using a grid for accuracy Average plant height was also determined. The results are shown in the following table:

| Treatment | Average Number Of Plants Emerged Per 100 Seeds Planted | Average Plant Height |
| --- | --- | --- |
| Material A | 70.3 | * |
| Material B | 59.3 | 4.3 |

| Treatment | Average Number Of Plants Emerged Per 100 Seeds Planted | Average Plant Height |
|---|---|---|
| Material C | 87.1 | 3.8 |

*Not measurable due to the twisting and contortion of the leaves.

Plant vigor or health is difficult to measure. However, if the plants treated with Material C (TBZ-Alder bark) were given an index of 100, the plants treated with Material B (TBZ-Douglas Fir bark) would be rated at 50, or half the vigor of the plants treated with the TBZ-Alder bark, and the plants treated with Material A (TBZ-Cyrus Talc BT 200) would be rated at less than 25.

The following is a summary of the daily observations made on these plants over the 16 days of the test.

Material A (TBZ-Cyrus Talc BT 200):

Initial germination started about three days after planting of the seeds. However, the plant growth and emergence was extremely variable.

The leaves of the plants showed some contortion and lack of chlorophyll as early as six days after planting. Spindliness was exaggerated by ten days.

At the end of the sixteen day period, the leaves were so contorted that plant height could not be evaluated. Plant germination continued throughout the 16 day test period, but normal plant growth was lacking.

Material B (TBZ-Fir Bark):

Initial germination started three days after planting of the seeds. Emergence was more erratic and less uniform when compared to Material C (TBZ-Alder bark). About 30% of the seed showed emergence at the end of the first three days. However, the plants showed lack of vigor and were more spindly when compared to the plants treated with Material C (TBZ-Alder bark).

Some plants showed exceptional length extension after ten days of growth, but these plants were not typical healthy wheat plants. Erratic emergence and growth continued throughout the sixteen day test period.

Material C (TBZ-Alder Bark):

Initial germination started three days after planting of the seeds. Approximately 30% of the seeds showed protrusion through the surface at this time.

At the end of ten days, 60% of the plants had germinated and were at an average height about 1-1.5 inches tall. Plants were very vigorous, had a good dark green color and emerged uniformly over the planted area.

The plants continued to grow steadily and remained vigorous throughout the test period of sixteen days.

EXAMPLE 8

The following compositions were prepared:

| Composition | Contents |
|---|---|
| A | 100% Comminuted Alder bark |
| B | 100% Comminuted Douglas fir bark |
| C | 68% Pyrax ABB, 2.7% Topsin-M, 29% Comminuted Alder bark |
| D | 68% Pyrax ABB, 2.7% Topsin-M, 29% Comminuted Douglas fir bark |
| E | 48% Cyprus Talc BT 200, 24% Zeolite, 2.7% Topsin-M, 24% Comminuted Alder bark |
| F | 48% Cyprus Talc BT 200, 24% Zeolite, 2.7% Topsin-M, 24% Comminuted Douglas fir bark |
| G | 54% Cyprus Talc BT 200, 8.4% Captan 90, 38% Comminuted Alder bark |
| H | 54% Cyprus Talc BT 200, 8.4% Captan 90, 38% Comminuted Douglas fir bark |
| I | 49% Cyprus Talc BT 200, 24% Zeolite, 0.5% Thiabendazole, 24% Comminuted Alder bark |
| J | 49% Cyprus Talc BT 200, 24% Zeolite, 0.5% Thiabendazole, 24% Comminuted Douglas fir bark |
| K | 57% Cyprus Talc BT 200, 28% Zeolite, 10% Maneb 80, 5% Comminuted Alder bark |
| L | 57% Cyprus Talc BT 200, 28% Zeolite, 10% Maneb 80, 5% Comminuted Douglas fir bark |

The pH of these materials was determined. The results are as follows:

| Composition | pH |
|---|---|
| A | 5.5 |
| B | 4.8 |
| C | 5.0 |
| D | 4.2 |
| E | 5.9 |
| F | 5.6 |
| G | 5.9 |
| H | 5.5 |
| I | 6.2 |
| J | 5.9 |
| K | 5.8 |
| L | 5.8 |

As can be seen, all of the materials are acidic.

Next, potting soil was sterilized by heating it for 45 minutes at 140° F. After cooling, the soil was adjusted to pH 7.0 using calcium carbonate and/or sulfuric acid.

Twelve ounces of this soil was placed in 3-pint capacity plastic pots. One hundred Derkwin Spring Wheat were placed on top of the soil in one-half of each pot, and 100 Klages Spring Barley seeds were placed in the other half. Next, one ounce of one of compositions A-L was placed over the seeds. Then, two ounces of sterilized soil were placed on top of the seeds.

Four ounces of water was added to each pot after planting of the seeds, and the pots were placed in a room where temperatures averaged 55°-60° F. Water was added at the rate of 4 ounces per pot during the test period when a minimum of 50% water holding capacity was reached (determined by a tensiometer).

Growth measurements were made 19 and 28 days after planting of the seeds. The results are shown in the following tables:

| | Day 19 After Planting | | | |
|---|---|---|---|---|
| | BARLEY | | WHEAT | |
| COMPOSITION | AVERAGE HEIGHT* | AVERAGE VIGOR* | AVERAGE HEIGHT* | AVERAGE VIGOR* |
| A | 3 | 4.5 | 3 | 4.5 |

-continued

| | Day 19 After Planting | | | |
| --- | --- | --- | --- | --- |
| | BARLEY | | WHEAT | |
| COMPOSITION | AVERAGE HEIGHT* | AVERAGE VIGOR* | AVERAGE HEIGHT* | AVERAGE VIGOR* |
| B | 2.25 | 2 | 2 | 2 |
| C | 2.75 | 3.5 | 2.75 | 3.5 |
| D | 3.5 | 4.5 | 3.5 | 4.5 |
| E | 3.5 | 4.5 | 3.5 | 4.5 |
| F | 3 | 4 | 2.75 | 4 |
| G | 3.75 | 4 | 2.75 | 4.0 |
| H | 2.75 | 2.5 | 2.25 | 2.5 |
| I | 3.5 | 4 | 3 | 4 |
| J | 3.25 | 3 | 3 | 3 |
| K | 3.25 | 2.5 | 2 | 2.5 |
| L | 2.25 | 2.5 | 2.25 | 2.5 |
| Untreated Control | 2.75 | 3.5 | 2.75 | 3.5 |

*NOTE:
Height: Height in inches measured from the pot rim.
Vigor: 1-5 rating. 1 = low vigor, 5 = highest vigor.

| | Day 28 After Planting Number of Plants Emerged Per 100 Planted | |
| --- | --- | --- |
| COMPOSITIONS | WHEAT | BARLEY |
| A | 94 | 92 |
| B | 94 | 81 |
| C | 91 | 85 |
| D | 95 | 92 |
| E | 96 | 85 |
| F | 96 | 91 |
| G | 90 | 95 |
| H | 98 | 96 |
| I | 97 | 90 |
| J | 87 | 88 |
| K | 91 | 83 |
| L | 96 | 73 |
| Untreated Control | 92 | 89 |

These results show that the compositions containing Alder bark, in most cases, produced a taller, more vigorous plant by 19 days after planting than did the compositions containing Douglas Fir bark. The number of plants emerged by day 28 was, in most cases, about the same for the compositions containing Alder bark as for corresponding compositions containing Douglas Fir bark.

EXAMPLE 9

The following materials were prepared, and the pH of each determined:

| Composition | Contents | pH |
| --- | --- | --- |
| A | 100% Comminuted Douglas Fir Bark | 4.8 |
| B | 100% Comminuted Alder Bark | 5.5 |
| C | 10% Comminuted Douglas Fir Bark + 90% Washed Sand | 4.4 |
| D | 10% Comminuted Alder Bark + 90% Washed Sand | 5.4 |
| E | 100% Washed Sand | 6.3 |

Twelve ounces of compositions A-E were placed in 3-pint capacity pots, and one hundred Derkwen wheat seeds were planted in each pot. The pots were watered, and the seeds grown under the same conditions as those described in Example 8.

Eight days after planting, the following measurements were obtained:

| Composition | Average Height | Average Vigor | Percent Germination |
| --- | --- | --- | --- |
| A | 0.5 in. | 1.0 | 17% |
| B | 1.0 in. | 2.5 | 60% |
| C | 1.0 in. | 4.0 | 70% |
| D | 1.25 in. | 4.0 | 60% |
| E | 3.0 in. | 5.0 | 75% |

Thirteen days after planting, the following measurements were obtained:

| Composition | Average Height | Average Vigor | Percent Germination |
| --- | --- | --- | --- |
| A | 1.0 in. | 1.0 | 27% |
| B | 1.5 in. | 2.5 | 87% |
| C | 2.5 in. | 4.0 | 88% |
| D | 3.5 in. | 3.5 | 98% |
| E | 5.0 in. | 2.0 | 91% |

Nineteen days after planting, the following measurements were obtained:

| Composition | Average Height | Average Vigor | Percent Germination |
| --- | --- | --- | --- |
| A | 1.5 in. | 1.0 | 36% |
| B | 3.0 in. | 2.0 | 87% |
| C | 4.0 in. | 3.0 | 89% |
| D | 6.0 in. | 4.5 | 98% |
| E | 6.0 in. | 4.0 | 88% |

The above experiment was repeated using the materials in place of A-E above:

| Material | Composition |
| --- | --- |
| F | 100% Comminuted Alder bark |
| G | 100% Comminuted Douglas Fir bark |
| H | 100% Comminuted Alder bark, pH adjusted to 7.0 using calcium carbonate and/or sulfuric acid |
| I | 100% Comminuted Douglas Fir bark, pH adjusted to 7.0 with calcium carbonate and/or sulfuric acid |
| J | Composition C from Example 8 (Topsin-M Alder bark) |
| K | Composition D from Example 8 (Topsin-M Douglas Fir bark) |

The following measurements were obtained:

| Composition | Day After Planting Wheat Seeds | Percent Germination | Average Height (in.) |
|---|---|---|---|
| F | 7 | 84 | <0.5 |
|   | 9 | 91 | <1.0 |
|   | 11 | 94 | 2.5 |
|   | 12 | 95 | 3.0 |
| G | 7 | 58 | <0.5 |
|   | 9 | 75 | <0.5 |
|   | 11 | 87 | 1.25 |
|   | 12 | 89 | 1.5 |
| H | 7 | 24 | <0.5 |
|   | 9 | 51 | <1.0 |
|   | 11 | 63 | 1.25 |
|   | 12 | 63 | 1.5 |
| I | 7 | 7 | <0.5 |
|   | 9 | 29 | <0.5 |
|   | 11 | 44 | <0.5 |
|   | 12 | 50 | <0.5 |
| J | 5 | 47 | — |
|   | 7 | 72 | 2.0 |
|   | 9 | 86 | 4.0 |
|   | 11 | 91 | 6.0 |
|   | 12 | 93 | 7.0 |
| K | 5 | 62 | — |
|   | 7 | 93 | 1.75 |
|   | 9 | 93 | 4.0 |
|   | 11 | 97 | 6.0 |
|   | 12 | 98 | 7.0 |

The results with compositions A-K show a clear superiority in perdent germination and plant height produced by the compositions containing Alder bark as compared to those containing Douglas Fir bark. Also, the compositions containing Alder bark generally produced more vigorous plants than did the compositions containing Douglas Fir bark.

PREPARATION AND USE OF SEED TREATMENT DUSTS COMPRISING COMMINUTED ALDER BARK

The seed treatment dusts of the present invention comprise: an active ingredient; a diluent material; and comminuted Alder bark. Comminuted Alder bark is used in the dusts as a diluent material, but it is a unique diluent material because of its ability to stimulate germination as well as to perform the other functions that a diluent material ordinarily performs. As discussed above, rapid germination is a key to producing healthy productive plants.

The active ingredients used in the dusts are those known in the art, and the amount of an active ingredient used in a dust is an effective amount. These amounts are also well known.

The diluent materials used are preferably the clays and talcs. The type and amount of diluent material and the amount of comminuted Alder bark used in a dust depends on a balancing of five factors: (1) cost; (2) abrasiveness; (3) flow characteristics; (4) dustiness; and (5) drying ability. Dusts of various compositions satisfying different needs can be prepared by appropriately balancing these factors. An ideal dust would be inexpensive, slightly abrasive and non-dusty, would flow freely and would have excellent drying ability.

The cost, abrasiveness and other properties of the clay and talc diluent materials are known. The following information about the properties of comminuted Alder bark is provided to aid in the formulation of seed treatment dusts.

Comminuted Alder bark is more costly, more abrasive, but less dusty than the clays and talcs. Further, comminuted Alder bark is a much better drying agent than are the clay and talc diluents. For example, under conditions of 50% relative humidity and temperatures in the range of 50° to 60° F., cut potato seeds dry in 2 to 2½ hours when dusted with a dust containing from about 25 to about 30% by weight of comminuted Alder bark. Under similar conditions, potato seeds dusted with a dust containing only talc or clay as the diluent material take 6 to 12 hours to dry. The faster drying time, as discussed above, translates into better disease control and less decay of seeds.

Adding up to about 40% by weight of comminuted Alder bark to a dust composed of clay and/or talc diluents improves the flow characteristics of the dust. If substantially more than 40% by weight of comminuted Alder bark is added to a dust, the dust will not flow freely and will clog the automated equipment usually used to dust and plant seeds. Further, the use of too much comminuted Alder bark in a dust causes the dust to be deposited nonuniformly on the seeds.

Accordingly, dusts of improved flow characteristics may be prepared by adding a small amount of comminuted Alder bark, usually from about 5 to about 10% by weight, to a dust otherwise composed of clay and talc diluents. Even better flow characteristics are obtained when from about 20 to about 40% by weight of comminuted Alder bark is added to the dusts, and the best flow characteristics are obtained when from about 25 to about 30% by weight of comminuted Alder bark is added to the dusts.

Dusts containing up to 40% by weight of comminuted Alder bark also cover seeds more uniformly and are more readily deposited on the seed than are dusts containing only clay and talc diluents. Using such dusts also prevents the buildup of dust which often occurs when dusts containing only clay and talc diluents are used since comminuted Alder bark is more abrasive than the clays and talcs and actually scrubs the machinery used to dust and plant seeds. Consequently, the use of dusts containing comminuted Alder bark increases planting efficiency since the use of these dusts decreases the number of instances where a planting machine becomes so clogged with dust that some seeds are not planted. The best coverage and deposition by dusts containing comminuted Alder bark and the best prevention of buildup occurs when dusts containing from about 20 to about 40%, and most preferably from about 25 to about 30%, by weight of comminuted Alder bark are used.

Once a dust has been formulated, the dust is blended. During the blending operation, the amounts of the diluent materials and of the comminuted Alder bark may have to be adjusted slightly as batches of materials vary in their moisture content. Since the moisture content greatly influences the flow and drying properties of the ingredients and of the dust, the relative amounts of each may have to be altered to obtain a dust having the proper flow and drying characteristics. Generally, the amount of each ingredient needs to be adjusted by no more than ±1%.

EXAMPLE 10

A fungicidal seed treatment dust useful for dusting potato seeds was prepared by mixing comminuted light Alder bark, Pyrax ABB and Topsin-M. Pyrax ABB is a clay having the following composition:

| | |
|---|---|
| SiO₂ | 80.61% |
| Al₂O₃ | 14.76% |
| Fe₂O₃ | 0.29% |
| Na₂O | 0.18% |
| K₂O | 1.38% |
| MgO | 0.02% |
| CaO | 0.02% |
| TiO₂ | 0.08% |
| Loss on ignition or oxidation | 2.68% |

Pyrax ABB was purchased from the Vanderbilt Co., 6279 Slausson Avenue, Los Angeles, Calif. 90040.

All of the ingredients were placed in a cylindrical dust blender, and the dust blender was rotated until the ingredients were thoroughly blended into a homogeneous mixture which took about 15–20 minutes. A total of one ton of potato fungicidal dust Was prepared, and the final proportions were: 68.2% by weight Pyrax ABB, 2.7% by weight Topsin-M and 29.1% by weight of comminuted Alder bark. This formulation is identified as Potato Dust I in the following discussion.

EXAMPLE 11

A second fungicidal dust useful for dusting potato seeds was prepared by mixing comminuted light Alder bark, Cyprus Talc BT 200, Zeolite and Topsin-M. All of the ingredients were added to a dust blender and were thoroughly blended as described in Example 10. A total of one ton of potato fungicidal dust was prepared. The final proportions were: 48.65% by weight Cyprus Talc BT 200, 24.32% by weight of Zeolite, 2.7% by weight Topsin and 24.32% by weight of comminuted Alder bark. This formulation is identified as Potato Dust II in the following discussion.

EXAMPLE 12

Another fungicidal dust useful for dusting potato seeds was prepared by mixing comminuted light Alder bark, Cyprus Talc BT 200 and Captan 90. The ingredients were mixed in a dust blender as described in Example 10. A total of one ton of potato fungicidal dust was prepared. The final proportions were: 54.0% by weight Cyprus Talc BT 200, 8.40% by weight Captan 90 and 38.00% by weight of comminuted Alder bark. This formulation is identified as Potato Dust III in the following discussion.

EXAMPLE 13

A fourth fungicidal dust useful for dusting potato seeds was prepared by mixing comminuted light Alder bark, Cyprus Talc BT 200, Zeolite and Thiabendazole. The Thiabendazole was formulated into a pre-mix which contained 20% of Thiabendazole and 80% of Cyprus Talc BT 200 by weight.

The comminuted Alder bark, pre-mix, Zeolite and Cyprus Talc BT 200 were added to a dust blender, and the ingredients were thoroughly blended as described in Example 10. A total of one ton of potato fungicidal dust was prepared, and the final proportions were: 48.72% by weight Cyprus Talc BT 200, 24.36% by weight of Zeolite, 2.55% by weight pre-mix (0.51% Thiabendazole) and 24.36% by weight of comminuted Alder bark. This formulation is identified as Potato Dust IV in the following discussion.

EXAMPLE 14

A fifth fungicidal dust useful for dusting potato seeds was prepared by mixing comminuted light Alder bark, Cyprus Talc BT 200, Zeolite and Maneb 80. Maneb 80 is a fungicide which is the coordination product of zinc ion and manganese ethylenebis(dithiocarbamate) which was purchased as a wettable powder concentrate having a guaranteed analysis of 80% from either DuPont, Wilmington, Del. or Rohm & Haas, Philadelphia, Pa.

The ingredients were mixed as described in Example 10. A total of one ton of potato fungicidal dust was prepared. The final proportions were: 57.15% by weight Cyprus Talc BT 200, 27.83% by weight of Zeolite, 10.03% by weight Maneb 80 and 4.97% by weight of comminuted Alder bark. This formulation is identified as Potato Dust V in the following discussion.

EXAMPLE 15

Potatoes which weighed 8 ounces each on average were cut into 4 sections each, each section being a potato seed. The cut potato seeds were fed into a Spudnik barrel-type potato seed treatment dust dispensing apparatus. Potato Dust I was also fed into the barrel portion through a dispensing orifice. Approximately 1 pound of Potato Dust I was used to dust each 100 pounds of potato seed. As the barrel of the Spudnik apparatus rotated, the potato seeds and dust were mixed by the spiral baffles inside the barrel, and the potato seeds were covered with Potato Dust I. The dusted seeds were removed from the barrel apparatus and placed in trucks or bags where they were stored until they were planted. The cut, dusted seeds were planted within six weeks of dusting.

Potato seeds were also cut, dusted with Potato Dusts II, III, IV and V and planted as described above.

Excellent results with all five potato fungicidal dust formulations were achieved. Potato seeds dusted with these dusts germinated rapidly, and the resultant plants were healthy and vigorous. Also stand counts were high when these dusts were used. Finally, workers using the dusts reported that the dusts possessed excellent flow characteristics and were less dusty than other dusts. The workers also reported that they had experienced no irritation from lignin slivers when using the dusts.

EXAMPLE 16

Potato seed pieces were dusted with Potato Dust II and a dust identical to Potato Dust II, except that Douglas Fir bark was used instead of Alder bark and coated calcium carbonate was used instead of Cyprus Talc BT 200 (hereinafter Potato Dust VI). The dusted potato seeds were planted 1 foot apart in rows 25 feet long, 4 rows per treatment. The plot was located near Redfield, Iowa.

Approximately four weeks after planting, the plants were rated for stand (number of plants emerging per 50 seed pieces planted). After harvesting, the potato crop was rated for overall yield and for the yield of potatoes greater than 2 inches in length. The results are presented in the following table:

| Treatment | Yield Total (cwt/A) | >2 Inches | Stand |
|---|---|---|---|
| Untreated Control | 257.0 | 161.9 | 22.25 |

| Treatment | Yield Total (cwt/A) | >2 Inches | Stand |
|---|---|---|---|
| Potato Dust IV (Topsin-M + Fir bark) | 251.2 | 176.5 | 22.00 |
| Potato Dust II (Topsin-M + Alder bark) | 278.1 | 185.9 | 22.50 |

As can be seen from the data, Potato Dust II (Topsin-M plus Alder bark) gave the highest total yield and yield of 2" or greater potatoes. Potato Dust VI containing Topsin-M and Douglas Fir bark had a yield slightly less than the untreated control.

EXAMPLE 17

A tests was conducted in North Dakota to determine the effects of the seed treatment dusts of the invention on the growth of potatoes. In these tests, potato seed pieces cut from Norgold Russet potatoes were treated with the following dusts: Potato Dust II (as prepared in Example 11); Potato Dust VI (See Example 16); Potato Dust III (as prepared in Example 12); and Potato Dust IV (as prepared in Example 13).

Potato seeds were cut and dusted with the various dusts and planted the following day. One batch was planted in early May (early trial), and another batch was planted 2 weeks later in May (late trial). The potato seeds were planted 1 foot apart in 50 foot rows; the rows were 38 inches apart. A total of four rows were planted for each treatment, and the plot was a randomized complete block.

The potatoes from both plantings were harvested four months after the first planting. Approximately six weeks after planting of each of the two groups, the potatoes were rated for stand counts, seed piece decay, plant vigor and the presence of certain diseases. After harvesting, the potato crop was rated for overall yield and for the yield of the various grades of potatoes.

The results are presented in the following Table. As can be seen from the data, the formulation containing Topsin-M and Alder bark (Potato Dust II) produced the highest yield for the early planted potatoes, while the formulation containing Topsin-M and Fir bark (Potato Dust VI) produced the highest yield for the late planted potatoes. There was very little difference in the final stand count between the various treatments. However, the formulation containing Topsin-M and Alder bark (Potato Dust II) gave the highest stand count for both planting dates compared to the Topsin-M and Fir bark formulation (Potato Dust VI).

With respect to decay (both soft rot and dry rot), the formulation containing Topsin-M and Alder bark (Potato Dust II) was better at controlling decay compared to the formulation containing Topsin-M and Fir bark (Potato Dust VI). This formulation also was better at controlling Rhizoctonia.

| Treatment | Total Yield (cwt/acre) | Yield Grade A (%) | Stand[1] | Vigor[2] | Decay[3] Index | Rhizoctonia[4] |
|---|---|---|---|---|---|---|
| Untreated control (early trial) | 215.1 | 53.9 | 45.0 | 3.42 | 3.80 | 30.1 |
| Potato Dust II (Topsin-M + Alder bark, early trial) | 225.2 | 55.8 | 48.2 | 3.67 | 0 | 9.3 |
| Potato Dust VI (Topsin-M + Fir bark, early trial) | 213.6 | 52.6 | 47.3 | 3.68 | 2.0 | 10.5 |
| Untreated control (late trial) | 227.3 | 51.0 | 48.3 | 3.80 | 0 | 11.1 |
| Potato Dust II (Topsin-M + Alder bark, late trial) | 223.7 | 48.1 | 49.2 | 3.80 | 0 | 5.7 |
| Potato Dust VI (Topsin-M + Fir bark, late trial) | 231.0 | 51.6 | 48.7 | 3.73 | 0.5 | 6.0 |
| Potato Dust IV (late trial) | 228.9 | 49.7 | 48.0 | 3.72 | 0 | 9.5 |
| Potato Dust III (late trial) | 227.9 | 52.2 | 48.0 | 3.70 | 0 | 11.0 |
| Comminuted Alder bark | 201.9 | 43.9 | 47.0 | 3.42 | 1.3 | 10.6 |

[1] Number of plants emerging per 50 potato seeds that were planted.
[2] Plants were rated 0–4 for vigor as follows: 1 = poor, 4 = good. The recorded number is the average of 40 plants per treatment (10 plants from each of the 4 replicate rows).
[3] Both soft rot and dry rot were rated 0–10 for decay as follows: 0 = no decay, and 10 = complete decay. The reported number is the combined soft rot and dry rot rating and is the average of 10 seed pieces per treatment (10 plants from each of the 4 replicate rows).
[4] Percent stems infected. Recorded number is average of 40 plants per treatment (10 plants from each of the 4 replicate rows).

EXAMPLE 18

Potato seed pieces cut from Russet Burbank potatoes were treated with various seed treatment compositions. All seed treatment compositions were applied at the rate of one pound per 100 pounds of seed potatoes. The freshly-cut seed pieces and the seed treatment compositions were placed into plastic bags simultaneously, and the bags shaken vigorously to help insure complete coverage.

For each seed treatment composition, fifty seed pieces were planted 12 inches apart in rows 50 feet long, with the rows 36 inches apart. The plot was a randomized complete block design with five replications for each treatment. The plot was located near Twin Falls, Id.

An additional plot was planted for use in the seed decay and stem number evaluations. Fifteen seed pieces for each treatment were planted in each of three replications.

Stand counts (the number of plants emerging per fifty seed pieces planted) were taken 27, 33, and 35 days after planting. The small plot used for decay evaluation and stem counts was hand-harvested ten weeks after planting, and the stems counts and decay evaluations performed. The seed pieces were evaluated for decay using the following scale:

1 = 0 to trace of decay
2 = trace to 25% of the surface decayed
3 = 25% to 50% of the surface decayed
4 = 50% to 75% of the surface decayed
5 = 75% to 100% of the surface decayed The main yield plot was harvested 4½ months after planting. The results are shown in the following table.

|  | Emergence ||| | | Yield ||
| Treatment | 27 days after planting | 33 days after planting | 35 days after planting | Decay Rating | Stems/ Hill | Total (cwt/ acre) | % U.S. #1 |
|---|---|---|---|---|---|---|---|
| Alder bark blank | 23.0 | 37.2 | 44.4 | 4.93 | 2.06 | 322 | 47.8 |
| Douglas Fir bark blank | 21.4 | 34.8 | 42.4 | 4.60 | 2.81 | 334 | 45.7 |
| Potato Dust IV (Thiabendazole + Alder bark) | 25.4 | 41.2 | 45.0 | 2.71 | 2.63 | 360 | 42.0 |
| Potato Dust II (Alder bark Topsin-M+ Alder bark) | 18.2 | 33.8 | 40.0 | 3.18 | 2.64 | 340 | 49.3 |
| Untreated Control | 31.2 | 40.0 | 46.2 | 4.63 | 2.66 | 378 | 49.2 |

These results show that Alder bark when used alone gave consistently better emergence than did Douglas Fir bark used alone. The yields obtained using these two treatments were similar.

EXAMPLE 19

The test of Example 18 was repeated with Potato Dust IV. The potato seeds were planted and stand counts were made 28 and 47 days after planting. Stem counts were made, and the seed pieces were evaluated for decay 49 days after planting. The potatoes were harvested four months after planting. The results of these tests are shown in the following table.

|  | Emergence || | | Yield ||
| Treatment | 28 days after planting | 47 days after planting | Stems/ Hill | Decay Rating | Total (cwt/A) | % U.S. #1 |
|---|---|---|---|---|---|---|
| Untreated Control | 9.4 | 47.2 | 2.2 | 2.7 | 385 | 58.3 |
| Potato Dust IV (Thiabendazole + Alder bark) | 20.6 | 48.6 | 3.3 | 1.9 | 334 | 54.5 |

None of the foregoing description of the preferred embodiments is intended in any way to limit the scope of the invention which is set forth in the following claims. Those skilled in the art will recognize that many modifications, variations and adaptations are possible.

I claim:

1. A method of using comminuted Alder bark as a stimulator of germination which comprises:
    dusting a seed with a material consisting essentially of comminuted Alder bark; and
    planting the dusted seed.

2. A method of using comminuted Alder bark as a stimulator of germination which comprises:
    planting a seed in a growth medium consisting essentially of comminuted Alder bark; and
    placing the growth medium containing the seed into an environment conducive to germination.

3. A synthetic growth medium consisting essentially of uncombusted comminuted Alder bark.

4. The growth medium of claim 3 wherein the Alder bark has a moisture content of from about 6 to about 11%.

5. The growth medium of claim 3 wherein the Alder bark has the consistency of a powder or dust.

6. The growth medium of claim 5 wherein the Alder bark meets the following standards:
    100% of the particles will pass through a 40 mesh screen;
    98% of the particles will pass through a 100 mesh screen; and
    91–97% of the particles will pass through a 200 mesh screen.

* * * * *

UNITED STATES PATENT AND TRADEMARK OFFICE
CERTIFICATE OF CORRECTION

PATENT NO. : 5,024,690

DATED : June 18, 1991

INVENTOR(S) : Charles C. Chollet

It is certified that error appears in the above-identified patent and that said Letters Patent is hereby corrected as shown below:

<u>IN THE REFERENCES CITED</u>

On the cover page, tenth entry of "U.S. REFERENCES CITED", please delete "71/79" and substitute therefor --504/260--.

<u>IN THE DETAILED DESCRIPTION OF PRESENTLY PREFERRED EMBODIMENTS</u>

In column 2, line 5, please delete "neWly" and substitute therefor --newly--.

In column 4, lines 24-29, please delete the chemical composition

"MgO: 30%
$SiO_2$: 60%
$Al_2O_3$: 0.5%
CaO: 2%
$Fe_2O_3$: 2%
Loss on ignition or oxidation: 5.5%"

and substitute therefor

| | |
|---|---|
| --MgO | 30% |
| $SiO_2$ | 60% |
| $Al_2O_3$ | 0.5% |
| CaO | 2% |
| $Fe_2O_3$ | 2% |
| Loss on ignition or oxidation | 5.5%-- |

UNITED STATES PATENT AND TRADEMARK OFFICE
CERTIFICATE OF CORRECTION

PATENT NO. : 5,024,690

DATED : June 18, 1991

INVENTOR(S) : Charles C. Chollet

It is certified that error appears in the above-identified patent and that said Letters Patent is hereby corrected as shown below:

In column 5, lines 4-16, please delete the chemical composition

"$SiO_2$: 69.60%
$Al_2O_3$: 11.30%
$K_2O$: 5.20%
$Fe_2O_3$: 1.84%
$Na_2O$: 1.04%
$CaO$: 1.00%
$MgO$: 0.36%
$TiO_2$: 0.30%
$BaO$: 0.20%
$MnO_2$: 0.01%
$P_2O_5$: 0.01%
$SiO_3$: 0.01%
$PbO$: 0.01%"

and substitute therefor

--$SiO_2$ 69.60%
$Al_2O_3$ 11.30%
$K_2O$ 5.20%
$Fe_2O_3$ 1.84%
$Na_2O$ 1.04%
$CaO$ 1.00%
$MgO$ 0.36%
$TiO_2$ 0.30%
$BaO$ 0.20%
$MnO_2$ 0.01%
$P_2O_5$ 0.01%
$SiO_3$ 0.01%
$PbO$ 0.01%--

UNITED STATES PATENT AND TRADEMARK OFFICE
CERTIFICATE OF CORRECTION

PATENT NO. : 5,024,690

DATED : June 18, 1991

INVENTOR(S) : Charles C. Chollet

It is certified that error appears in the above-identified patent and that said Letters Patent is hereby corrected as shown below:

In column 5, line 33, please delete "bounds" and substitute therefor --pounds--.

In column 6, line 14, please delete "da-s" and substitute therefor --days--.

In column 6, line 32, please delete "B" and substitute therefor --8--.

In column 6, line 60, after "accuracy" please insert --.--.

In column 7, line 20, please delete "was" and substitute therefor --were--.

In column 9, line 63, please delete "Derkwen" and substitute therefor --Derkwin--.

In column 11, line 29, please delete "perdent" and substitute therefor --percent--.

In column 13, line 19, please delete "Was" and substitute therefor --was--.

In column 13, line 34, please delete "Topsin" and substitute therefor --Topsin-M--.

In column 15, line 18, please delete "tests" and substitute therefor --test--.

UNITED STATES PATENT AND TRADEMARK OFFICE
CERTIFICATE OF CORRECTION

PATENT NO. : 5,024,690

DATED : June 18, 1991

INVENTOR(S) : Charles C. Chollet

It is certified that error appears in the above-identified patent and that said Letters Patent is hereby corrected as shown below:

In column 15, line 53, please delete "See" and substitute therefor --see--.

In column 17, line 7, please delete "stems" and substitute therefor --stem--.

Signed and Sealed this

Ninth Day of August, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO.   : 5,024,690
DATED        : June 18, 1991
INVENTOR(S)  : CHOLLET

It is certified that error appears in the above-indentified patent and that said Letters Patent is hereby corrected as shown below:

Column 2, line 61, add --slivers-- after "lignin".

Signed and Sealed this

Sixth Day of December, 1994

Attest:

BRUCE LEHMAN

Attesting Officer

Commissioner of Patents and Trademarks